United States Patent [19]
Connor et al.

[11] Patent Number: 5,398,689
[45] Date of Patent: Mar. 21, 1995

[54] ULTRASONIC PROBE ASSEMBLY AND CABLE THEREFOR

[75] Inventors: Brian G. Connor, Stratham, N.H.; Thomas P. Stephens, Boxford, Mass.; David P. Dolan, Londonderry, N.H.; Thomas A. Shoup, Lowell, Mass.

[73] Assignee: Hewlett-Packard Company, Palo Alto, Calif.

[21] Appl. No.: 78,129

[22] Filed: Jun. 16, 1993

[51] Int. Cl.$^6$ ............................................. A61B 8/00
[52] U.S. Cl. ................... 128/662.03; 128/4; 128/662.06
[58] Field of Search ............... 128/660.07, 660.01; 310/334; 439/55, 496

[56] References Cited

U.S. PATENT DOCUMENTS

| | | | |
|---|---|---|---|
| 3,086,071 | 4/1963 | Preston | 174/117 |
| 3,168,617 | 2/1965 | Richter | 174/117 |
| 3,818,117 | 6/1974 | Reyner, II et al. | 174/36 |
| 3,876,964 | 4/1975 | Balaster et al. | 333/84 |
| 4,305,014 | 12/1981 | Borburgh et al. | 310/334 |
| 4,375,818 | 3/1983 | Suwaki et al. | 128/660 |
| 4,435,614 | 3/1984 | McAusland | 174/117 PC |
| 4,543,960 | 10/1985 | Harui et al. | 128/660 |
| 4,902,236 | 2/1990 | Hasircoglu | 439/77 |
| 4,913,662 | 4/1990 | Noy | 439/490 |
| 4,928,699 | 4/1990 | Sasai | 128/662 |
| 4,989,582 | 2/1991 | Sakiyama et al. | 128/6 |
| 4,996,974 | 3/1991 | Ciarlei | 128/4 |
| 5,044,053 | 9/1991 | Kopel et al. | 29/25.35 |
| 5,126,616 | 6/1992 | Gorton et al. | 310/334 |
| 5,176,142 | 1/1993 | Mason | 128/662.06 |
| 5,181,514 | 1/1993 | Solomon et al. | 128/660.09 |
| 5,213,103 | 5/1993 | Mortin et al. | 128/660.07 |
| 5,276,455 | 1/1994 | Fitzsimmons ewt al. | 343/777 |

FOREIGN PATENT DOCUMENTS 0320331  11/1988  European Pat. Off.
WO92/02180  2/1992  WIPO .

OTHER PUBLICATIONS

Bom, N. et al., *International Journal of Cardiac Imaging*, 4:79-88 (1989) "Early and recent intraluminal ultrasound devices".

Axon' Cable Inc. "The Ultimate Connection with Flat Flex Cables by Axon'".

Sanders Associates, Inc., "Flexible Printed Wiring in all lengths for all layouts", Mar. 14, 1958—Electronics engineering edition, p. 20.

Tape Cable, Division of Burndy Corporation "Technical Bulletin 18" 50M2X25 Series Flat Signal Cable.

Hanrath, P. et al., "Tansesophageal Echo Cardiograph" Cardiology Dept., 2nd Medical Clinic, Eppendorf University Hospital, Martinistrasse 52 Hamburg.

*Primary Examiner*—Francis Jaworski

[57] ABSTRACT

An ultrasonic probe including a sensor head having an array of ultrasonic transducer elements is disclosed. The sensor head is located at the tip of a flexible shaft. The flexible shaft houses a flex circuit which is electrically connected directly to the transducer elements. The flex circuit transmits electrical signals from the transducer elements to the handle of the probe. The flexible shaft is bendable in all directions and can bend in a sharp radius in the region near the tip of the flexible shaft.

11 Claims, 6 Drawing Sheets

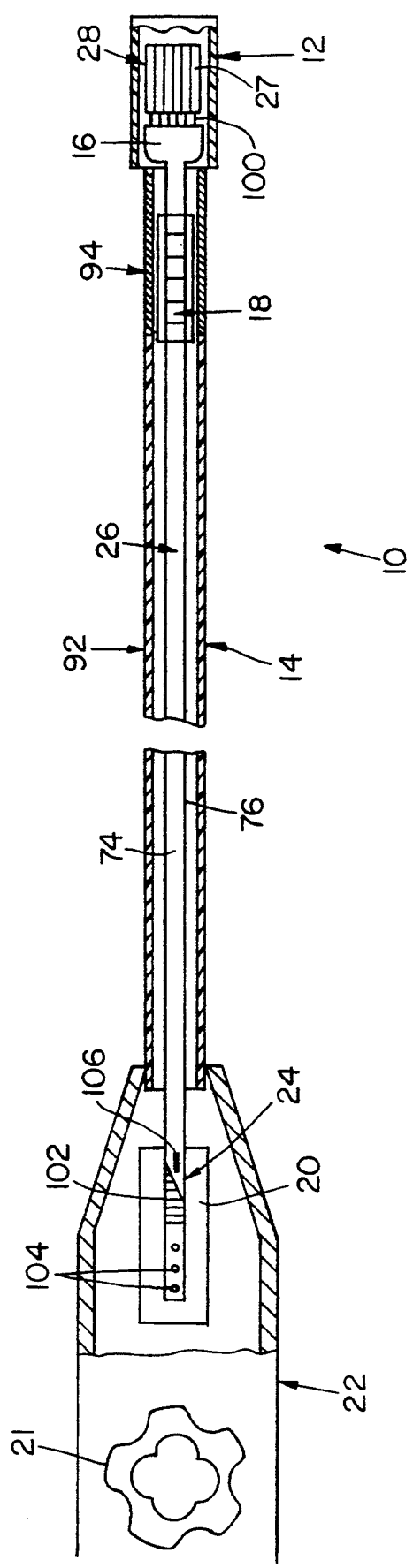

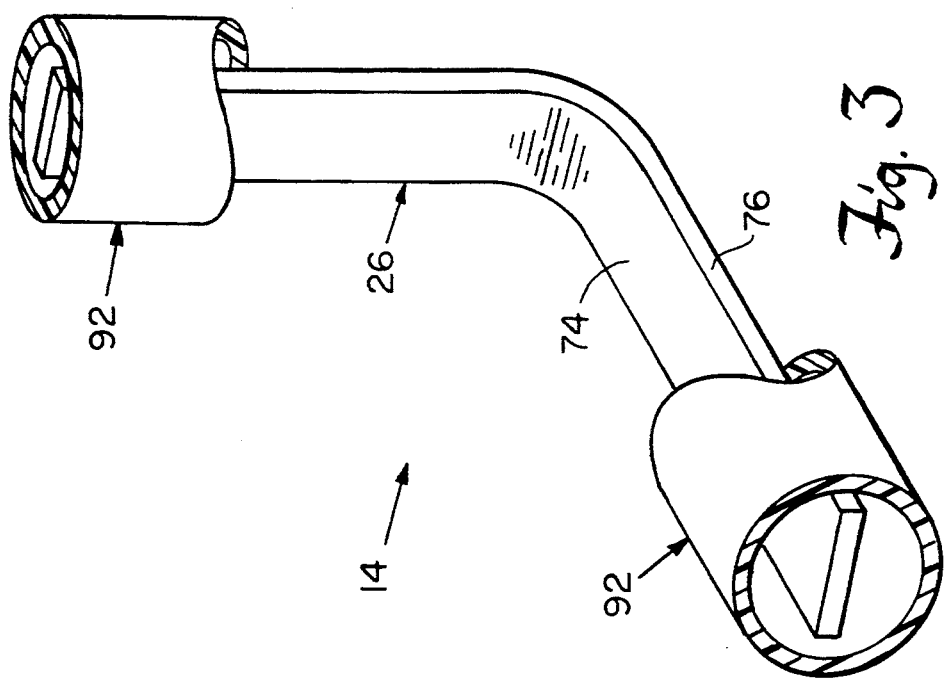
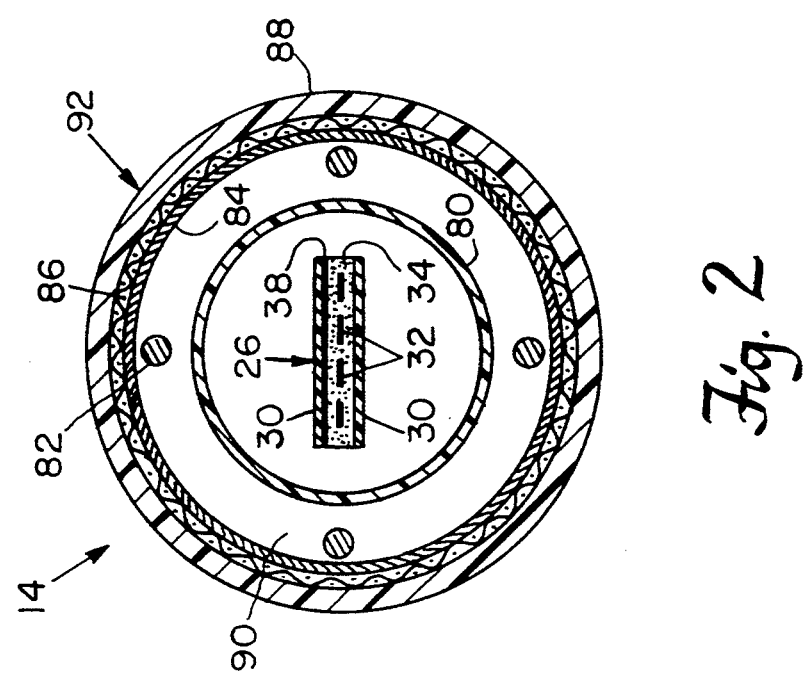

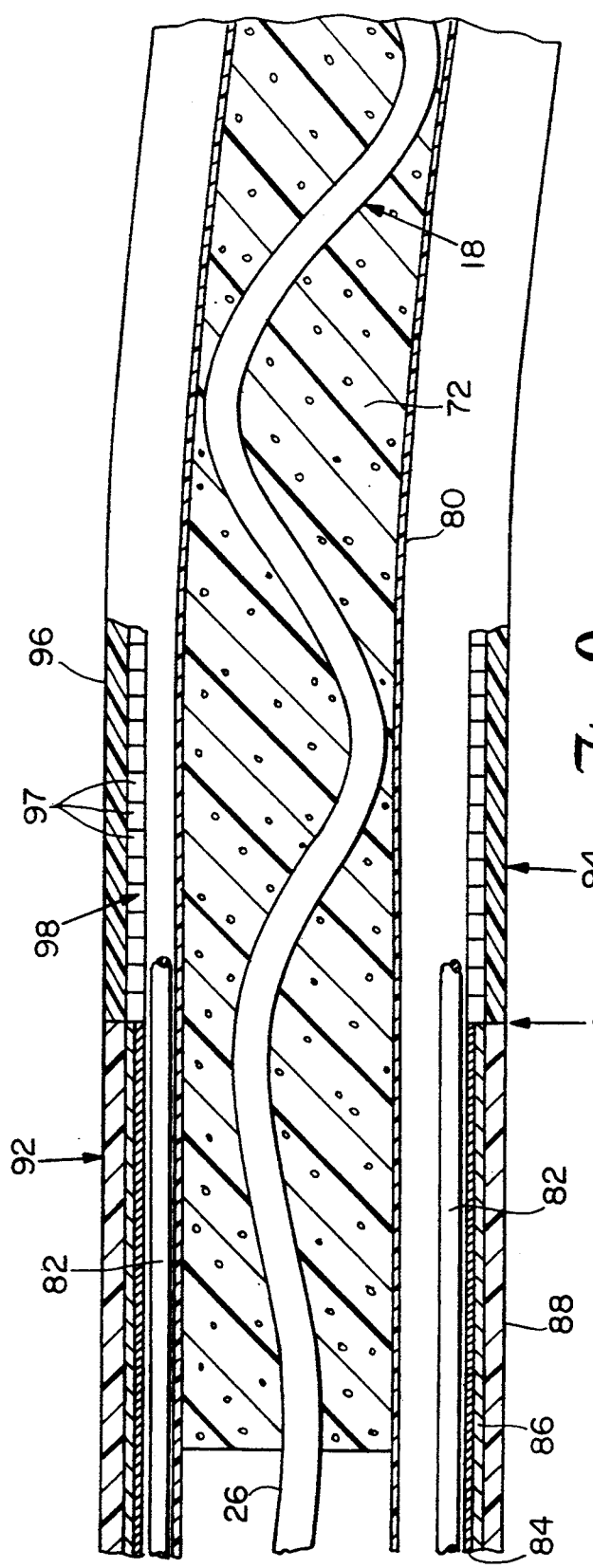
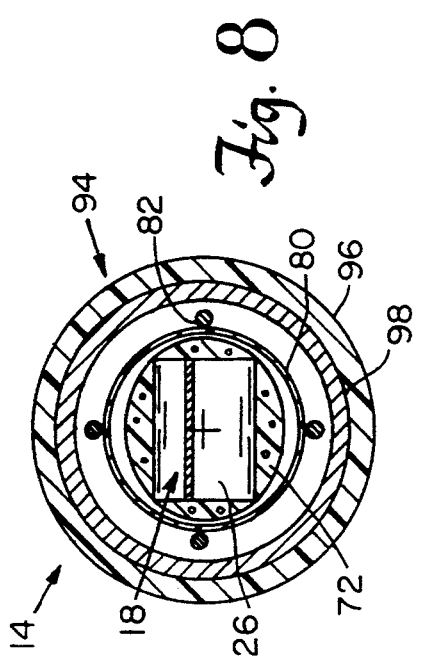

ULTRASONIC PROBE ASSEMBLY AND CABLE THEREFOR

BACKGROUND OF THE INVENTION

Ultrasonic endoscope probes are used to monitor internal regions of a patient, for example, organs such as the heart. An ultrasonic endoscope typically includes a shaft for insertion into body cavities of a patient such as the esophagus. At the tip of the shaft is a sensor head containing an array of ultrasonic sensor elements for monitoring internal organs. The sensor elements are electrically connected to an intermediate circuit housed in the sensor head by a short flexible circuit or a connector. A coaxial cable is electrically connected to the intermediate circuit and transmits electrical signals through the shaft between the sensor elements and the handle of the probe. The probe handle controls the operation of the endoscope.

The intermediate circuit or connector adds to the size of the sensor head. Some sensor heads having intermediate circuits, especially high density sensor heads with a large number of ultrasonic transducer elements, are too large for insertion into small body cavities such as a child's esophagus.

There is a continuing need for an ultrasonic sensor endoscope having a reduced size sensor head. Additionally, the diameter of the shaft must be small enough for insertion into small body cavities. Furthermore, the shaft should be flexible in all directions and also capable of being bent in a sharp radius in the region close to the sensor head in order to negotiate tight curves in body cavities. This allows the sensor head to be positioned for diagnostic utility. Further, even in non-endoscopic applications such as a transthoracic probe, cables are typically thick and somewhat cumbersome due to the lack of flexibility.

SUMMARY OF THE INVENTION

The present invention provides an ultrasonic probe suitable for use in varied configurations such as in a transthoracic, a transesophageal or an intravascular probe. The present invention includes a sensor head having an array of ultrasonic transducer elements. The sensor head is connected to a flexible cable at an end of the flexible cable. The flexible cable has a high density flex circuit with conductor traces leading through the flexible cable to the transducer element. The conductor traces of the flex circuit are between planar dielectric layers, and the traces conduct electrical signals between the transducer elements and the handle of the probe or ultrasound scanner. A flat flex circuit would not have been considered appropriate for a cable which requires bending in all directions; however, in accordance with one aspect of the present invention a flex cable having such bendability is provided.

The conductor traces of the flex circuit may be connected directly to the ultrasonic transducer elements thereby eliminating the need for an intermediate means of connection. This reduces the size of the sensor head to a size suitable for applications such as those involving insertion into small body cavities.

Additionally, relative to coaxial cables, the use of a flex circuit reduces the diameter of the cable and provides a means to more easily control the capacitance. In some applications, the capacitance can be used to improve the acoustic sensitivity and bandwidth of the transducer elements.

Also, the novel flex circuit described below provides improved flexibility of ultrasound probe cables, facilitating positioning of the probe by the operator.

In the preferred embodiment, the flex circuit is surrounded by an inner sheath inside an endoscope shaft and is slidable within the inner sheath such that the flex circuit is free to twist with bending of the shaft over a large bend radius. A portion of the flex circuit near the sensor head may be folded as in pleats, helically wound or otherwise shaped such that it is bendable in all directions in the region near the sensor head over a small bend radius. The shaped portion of the flex circuit allows the probe to negotiate tight curves such as in small body cavities. The shaped portion of the flex circuit is encapsulated in flexible material to evenly distribute the stresses caused by bending. Control wires extend the length of the endoscope shaft about the sheath and control the bending of the length of the shaft near the sensor head. An outer sheath surrounds the inner sheath and control wires. A braided sheath covers and provides torsional support for the outer sheath. Finally, a polymer extrusion covers the braided sheath to provide a smooth, watertight surface for the flexible endoscope shaft.

BRIEF DESCRIPTION OF THE DRAWINGS

The foregoing and other objects, features and advantages of the invention will be apparent from the following more particular description of preferred embodiments of the drawings in which like reference characters referred to the same parts throughout the different views. The drawings are not necessarily to scale, emphasis instead being placed upon illustrating the principles of the invention.

FIG. 1 is a sectional view of the present invention flexible endoscope probe.

FIG. 2 is a cross sectional view of the flexible endoscope shaft.

FIG. 3 is a perspective view of the flexible shaft in a first bent position with a portion of the sheathing broken away.

FIG. 8 is a cross-sectional view of shaft 14 showing the encapsulated pleats.

FIG. 9 is an enlarged sectional view of the shaft construction in the region about the pleated section.

DETAILED DESCRIPTION OF THE PREFERRED EMBODIMENT

Figure 4:
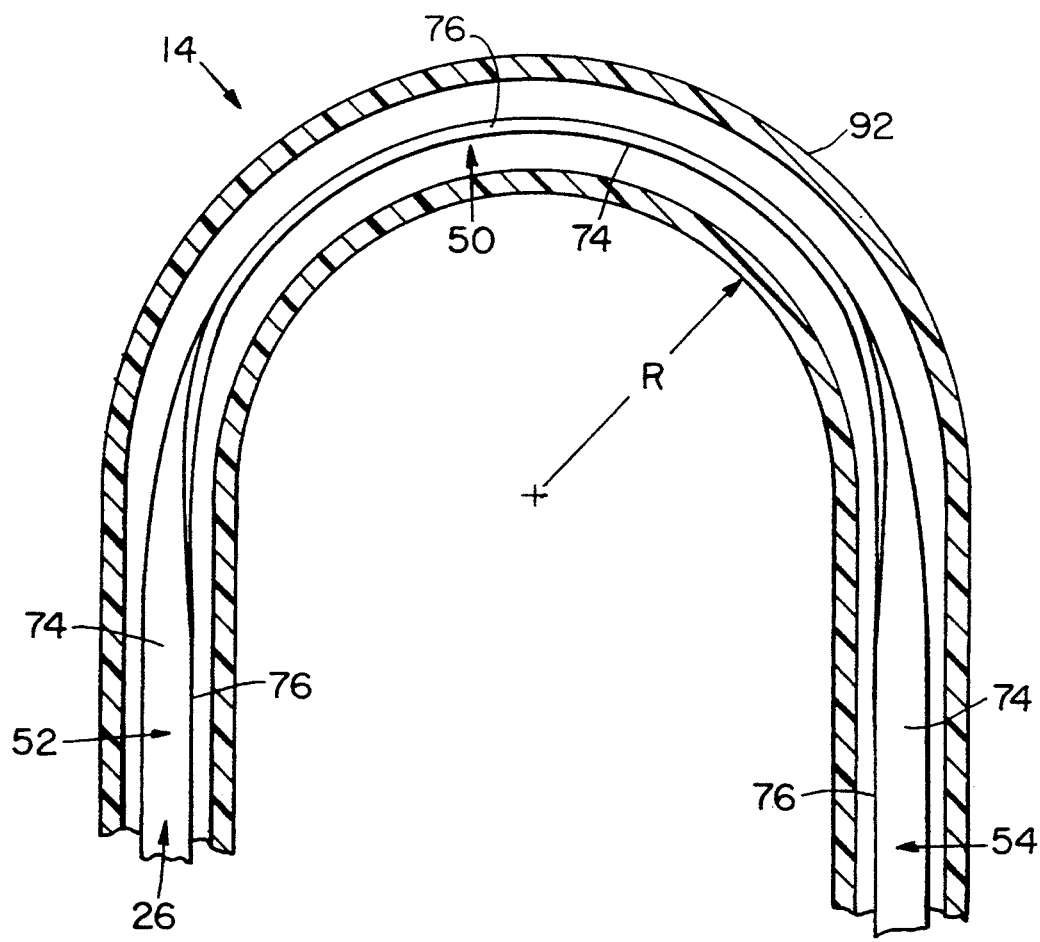
FIG. 4 is a sectional view of a portion of the flexible shaft in a second bent position.

In FIG. 1, ultrasonic endoscope probe 10 has a sensor head 12 containing an array 28 of ultrasonic transducer elements 27 for imaging internal regions of a patient, such as body organs. Sensor head 12 is connected to a probe handle 22 by a flexible shaft 14. The flexible shaft 14 has a protective waterproof region 92 surrounding a high density flex circuit 26. Flex circuit 26 electrically connects transducer elements 27 to circuit board 20 located in probe handle 22. Flexible shaft 14 is sealed to sensor head 12 and probe handle 22 to prevent moisture from entering any of those components. The sensor head 12 and flexible shaft 14 of probe 10 is inserted into body cavities of a patient and is suitable in varied configurations for transthoracic, transesophageal, or intravascular ultrasound applications. Flexible shaft 14 can be bent to follow the contours of body cavities and the bending is controlled by a control device 21 located at probe handle 22.

The number of transducer elements 27 in sensor head 12 can vary and is limited by the size of the sensor head 12 which also can vary. The size of sensor head 12 is limited by the size of the particular body cavity into which sensor head 12 is to be inserted. For example, a sensor head which is to be inserted into a child's esophagus must be smaller than a sensor head which is to be inserted into an adult's esophagus.

Often, a large number of transducer elements are preferred over a small number of sensor elements at the same inter-element spacing because of increased imaging performance. For example, a sensor head containing an array of 64 transducer elements typically performs better than a sensor head containing an array of 24 transducer elements. Additionally, a second array of transducer elements can be added to sensor head 12, in which the second array is rotated with respect to array 28. The two arrays can produce images in two orthogonal planes and further increase the performance of probe 10.

Conductor tabs 100 of interconnect 16 provide the electrical connection between the transducer elements 27 and conductor traces 32 (FIG. 2) in flex circuit 26. Tabs 100 are made of electro deposited gold over copper and are bonded directly to the transducer elements 27. Alternatively, tabs 100 may be formed by etching copper off interconnect 16. A tape automated bond (TAB) process or other operation is performed to make the electrical connection between array 28 and tabs 100.

By connecting tabs 100 directly to the transducer elements 27, the need for an intermediate circuit board or connector between the transducer elements 27 and the flex circuit 26 is eliminated. The elimination of these elements reduces the size of sensor head 12 as well as the amount of labor required to electrically connect transducer elements 27 to flex circuit 26. The decrease in the size of sensor head 12 allows sensor head 12 to be inserted into body cavities which are too small for the insertion of a larger sensor head which may contain an intermediate circuit board. Additionally, the elimination of the intermediate circuit board allows a greater number of ultrasonic transducer elements 27 to be added to sensor head 12 while maintaining a small sensor head size. It should be appreciated, however, that the present invention is applicable to embodiments using such intermediate connections.

Interconnect 24 of flex circuit 26 electrically connects flex circuit 26 to circuit board 20 which is located within probe handle 22. Circuit board 20 is an intermediate electrical junction from which a second cable electrically connects circuit board 20 to electronics including a monitor (not shown). A series of holes 104 secure and align interconnect 24 on circuit board 20. Signal pads 102 on interconnect 24 electrically connect the conductor traces 32 (FIG. 2) of flex circuit 26 to corresponding electrical contacts located on circuit board 20. Ground pad 106 provides an electrical connection for ground plane 38 (FIG. 2) to circuit board 20.

Signal pads 102 and ground pad 106 are mass reflow soldered to circuit board 20.

The construction of flexible shaft 14 and shaft region 92 is depicted in FIG. 2. The design of flexible shaft 14 is necessitated by the high aspect ratio of flex circuit 26 where flex circuit 26 is wide and thin (oblate). Flex circuit 26 occupies the central cavity of flexible shaft 14. Metallic conductor traces 32 of flex circuit 26 transmit electrical signals between transducer elements 27 (FIG. 1) and circuit board 20 located in probe handle 22. In the preferred embodiment, flex circuit 26 is a high density flexible circuit having thirty-four conductor traces 32 and is approximately 3/16 inches wide. Alternatively, the number of conductor traces 32 and width of flex circuit 26 can vary. Additionally, more than one flex circuit 26 can be used to transmit the electrical signals.

The conductor traces 32 are embedded in adhesive 34 and sandwiched between two insulating dielectric layers 30 which are typically polyimide film. In the preferred embodiment, a metallic ground plane 38 together with conductor traces 32 forms a strip line or microstrip type of transmission line. In the alternative, a series of metallic ground traces can be spaced between the conductor traces 32 to form an alternative type of transmission line. To someone skilled in the art, other obvious combinations of traces 32 and ground traces can be positioned to form well-known types of transmission lines with similar electrical properties to those types of transmission lines described here.

Flex circuit 26 is housed within a sheath 80 of expanded polytetrafluoroethylene (PTFE). PTFE sheath 80 provides a smooth, slippery surface within which flexible circuit 26 can twist and slide. Additionally, more than one flex circuit 26 can be housed within PTFE sheath 80 by stacking the circuits on top of each other. Alternatively, sheath 80 can be made of other polymers such as polyurethane.

Four guidewires 82 surround PTFE sheath 80 and are used to control the bending of flexible shaft 14. The distal end of flexible shaft 14 will bend in the direction in which a particular guidewire 82 is shortened. The more a particular guidewire is shortened, the more flexible shaft 14 will bend. The lengthening and shortening of guidewires 82 are controlled at probe handle 22 by a control mechanism 21.

A helical wound flat spring wire tube 84 surrounds guidewires 82 and provides electrical isolation and structural protection for flex circuit 26. Wire tube 84 is made from aluminum and plated through a hard anodize process with PTFE, to provide surface lubricity so that guidewires 82 can slide within wire tube 84. Alternatively, wire tube 84 can be made of other electrically conductive metals.

A woven braid 86 of stainless steel covers the exterior of tube 84 and provides torsional support for flexible shaft 14. Alternatively, woven braid 86 may be a tin copper alloy. Outer jacket 88, a urethane extrusion, covers woven braid 86 and provides a smooth, slippery, waterproof surface so that flexible shaft 14 can slide easily within body cavities of a patient. In the alternative, outer jacket 88 can be made of other biocompatible polymers.

The use of high density flex circuit 26 within flexible shaft 14 allows the diameter of flexible shaft 14 to be small. In the preferred embodiment, the outer diameter of flexible shaft 14 can be as little as 8 mm which permits probe 10 to be inserted into small body cavities. Additionally, the use of flex circuit 26 provides control of capacitance in shaft 14 which tunes the acoustic sensitivity of transducer elements 27.

FIGS. 3 and 4 depict the manner in which flexible shaft 14 bends. In FIG. 3, a section of flexible shaft 14 is bent in the direction normal to the flat surface 74 of flexible circuit 26. Flex circuit 26 is oriented within shaft region 92 so that flat surface 74 is facing the direction of the bend. Flex circuit 26 will only bend in the direction of flat surface 74 and will not bend in the direction normal to edge 76. However, flex circuit 26 is not always initially oriented within shaft region 92 so that flat surface 74 will face the direction of the bend. Therefore, in order for flexible shaft 14 to be bendable in all directions without damaging the flex circuit 26, the flex circuit is allowed to move, thereby, reorientating itself within shaft region 92 as depicted in FIG. 4.

In FIG. 4, flexible shaft 14 is bent in a radius R. Often, flex circuit 26 is oriented within shaft region 92 in a manner so that flat surface 74 is not facing the direction in which shaft 14 is to be bent. When shaft 14 is bent, flex circuit 26 moves within shaft region 92 so that section 50 of flex circuit 26 is reoriented in a twisted position. In this twisted position, flat surface 74 in section 50 faces the direction of the bend, thereby permitting flex circuit 26 to bend within shaft region 92. Sections 52 and 54 of flexible circuit 26 which are distant from the bent region remain untwisted.

Figure 5:
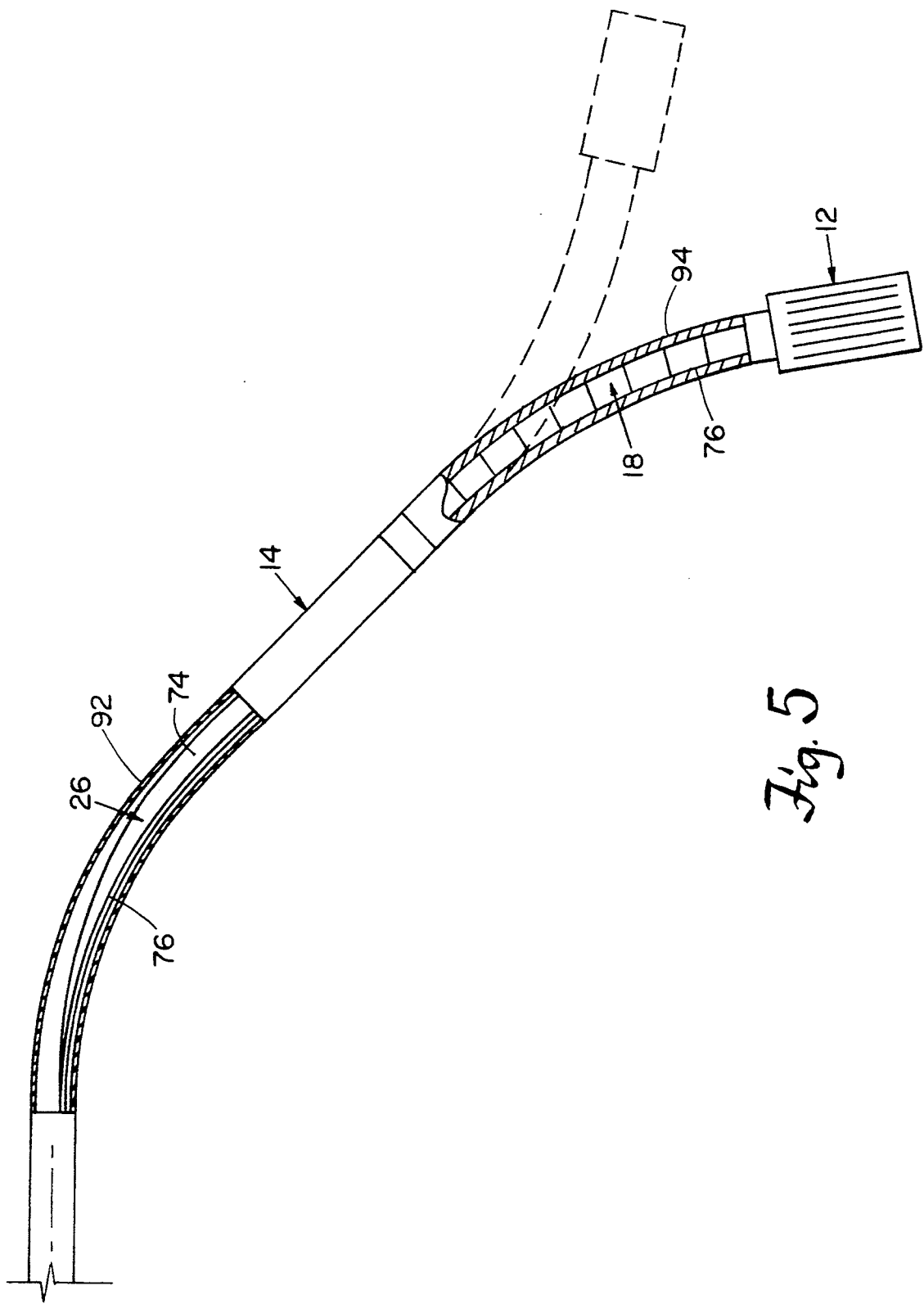
FIG. 5 is a sectional view of the flexible shaft in which the pleated section is bent in the direction normal to the edge of the flex circuit.

Referring to FIG. 5, pleated section 18 allows flexible shaft 14 to bend in the region near sensor head 12 in the direction normal to edge 76. Without pleated section 18, flexible shaft 14 would be unable to bend in that direction near sensor head 12 because flex circuit 26 is unable to twist near sensor head 12.

Figure 6:
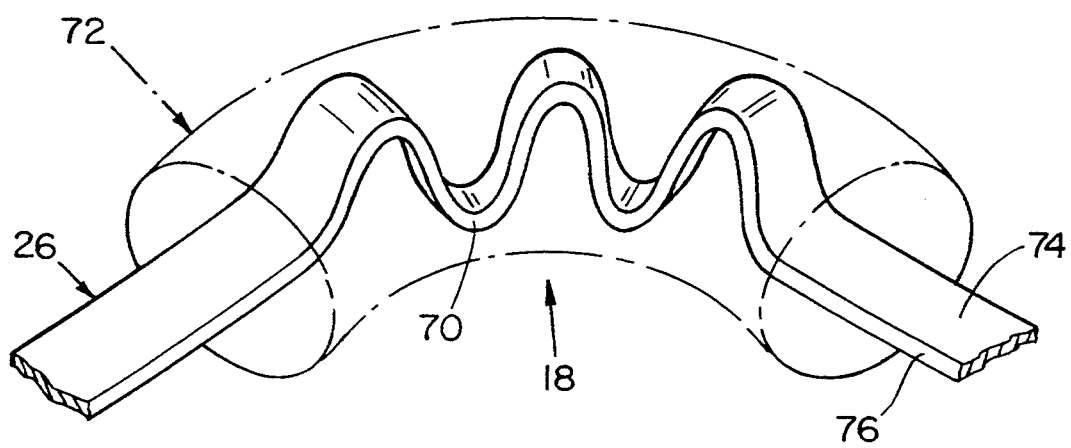
FIG. 6 is a perspective view of the pleated section of the flex circuit.
Figure 7:
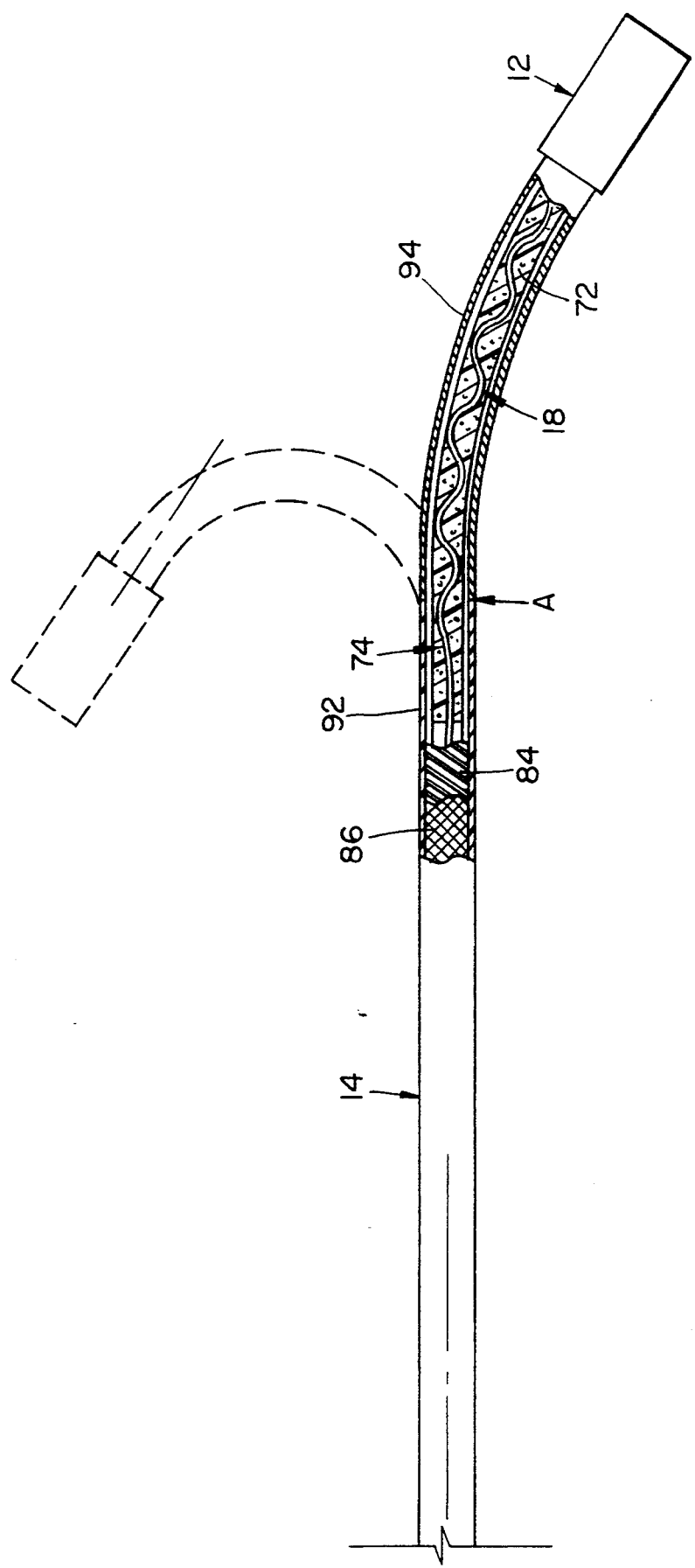
FIG. 7 is a sectional view of the flexible shaft in which the pleated section is bent in the direction normal to the planar surface of the flex circuit.

Referring to FIG. 6, the pleated section 18 of flex circuit 26 is shaped into a series of sinusoidal shaped pleats 70 formed by a pleating tool. In a preferred embodiment, the pleats have a pitch of 0.118 inches and a height of 0.07 inches. The pleats 70 allow flex circuit 26 to bend in the axis normal to edge 76 without twisting flex circuit 26. Additionally, pleated section 18 can bend in all directions as well as the direction normal to flat surface 74 as depicted in FIG. 7. If more than one flex circuit 26 is required, multiple flex circuits can be pleated simultaneously so that the pleats 70 will match when the circuits are stacked on one another. In addition, the pleating pitch and height may be varied to tailor the degree of flexibility. A fine pitch and large pleat height increases the flexibility of flex circuit 26 in the direction normal to edge 76.

The pleats 70 are encapsulated in a polyurethane sheath 72. The sheath 72 is cast around pleats 70 with a mold and in the preferred embodiment sheath 72 has an oval cross-section as depicted in FIG. 8. Alternatively, sheath 72 can have other cross-sectional shapes such as circular or rectangular cross-sections. A thin walled urethane tube may be used as the casting form and left intact providing a simple mold shape and enhancing the flex cable strength. Additionally, pleats 70 can also be encased in a hollow tube without encapsulation. The polyurethane sheath 72 distributes stresses on pleats 70 caused by bending to prevent stress concentrations from forming in the pleats 70. The reduction of stress concentrations increases the flex life of pleated section 18, which is the number of bending cycles pleated section 18 can endure before failure. Alternatively, other elastomers can be used to encapsulate pleats 70. When encapsulating the pleats 70 of multiple flex circuits 26, the encapsulating material must not bond the pleats 70 of adjacent flex circuits 26 together in order to maintain flexibility of pleated section 18.

Referring to FIGS. 7, 8 and 9, shaft region 92 terminates at location "A" of pleated section 18. Shaft region 92, which is previously discussed in greater detail above, houses flex circuit 26 within PTFE sheath 80. Guidewires 82 surround PTFE sheath 80 and are in turn surrounded by helical wound flat spring wire tube 84. Woven braid 86 covers the exterior of tube 84 and outer jacket 88 covers woven braid 86.

Bending neck region 94 is more flexible than region 92 and surrounds pleated section 18 from location "A" to sensor head 12. Bending neck region 94 allows pleated section 18 which is encapsulated in sheath 72 to bend in a sharper radius than sections of shaft 14 covered by region 92 (as depicted in FIG. 7). By allowing the region near sensor head 12 to bend in a sharper radius, sensor head 12 can negotiate tight curves within small body cavities with more ease and can also align the sensor head 12 as needed for diagnostic positioning.

Bending neck region 94 consists of flex linkage 98 and outer cover 96. Flex linkage 98 is made of a series of metallic links 97 which are connected together by rivets. Alternatively, links 97 can be made of nonmetallic materials and connected by other conventional means. Outer cover 96 is made of flexible, waterproof material such as neoprene or synthetic rubber.

Equivalents

While this invention has been particularly shown and described with references to preferred embodiments thereof it will be understood by those skilled in the art that various changes in form and details may be made therein without departing from the spirit and scope of the invention as defined by the appended claims. For example, the probe need not be endoscopic.

We claim:
1. An ultrasonic probe comprising:
a sensor head having an array of ultrasonic transducer elements therein; and
a flexible cable connected to the sensor head at an end thereof for enabling placement of the sensor head relative to a patient, the cable comprising a planar flex circuit having conductor traces leading through the flexible cable to the transducer elements, the conductor traces of the planar flex circuit connecting the transducer elements to a connector remotely located away from the sensor head, and a sheath surrounded the flex circuit along at least a portion of a length of the cable, at least a portion of the flexible cable being configured such that it is bendable in all directions.

2. A probe as claimed in claim 1 wherein at least a portion of the flex circuit is shaped such that it is bendable in all directions.

3. A probe as claimed in claim 2 wherein the shaped portion of the flex circuit is folded such that it is bendable in all directions.

4. A probe as in claim 2 wherein the shaped portion of the flex circuit is near the sensor head.

5. A probe as claimed in claim 2 wherein the shaped portion of the flex circuit is encapsulated in flexible material.

6. A probe as claimed in claim 2 wherein the flex circuit is free to move within the sheath such that the flex circuit is free to twist with bending of the cable.

7. A probe as claimed in claim 1 wherein the flex circuit is free to move within the sheath such that the flex circuit is free to twist with bending of the cable.

8. A probe as claimed in claim 1 wherein the cable comprises more than one planar flex circuit.

9. A probe as claimed in claim 1 wherein at least a portion of the flex circuit near the sensor head being shaped and encapsulated in flexible material along a first length of the cable such that the cable is bendable along the first length in all directions with expansion and contraction of flex circuit folds, the sheath being an inner sheath surrounding the flex circuit along a second length of the cable, the flex circuit being free to move within the inner sheath such that the flex circuit is free to twist with bending of the second length, the ultrasonic probe further comprising:

control wires about the inner sheath extending through the cable for controlling bending of the first length of the cable; and an outer sheath about the control wires and inner sheath.

10. A probe as claimed in claim 9 wherein the cable includes more than one planar flex circuit.

11. A probe as claimed in claim 9 wherein the planar flex circuit connects the sensor head to a connector.

* * * * *